(12) United States Patent
Das (10) Patent No.: US 8,128,685 B2
(45) Date of Patent: Mar. 6, 2012

(54) BIFURCATED STENTING APPRATUS AND METHOD

(75) Inventor: Gladwin S. Das, Arden Hills, MN (US)

(73) Assignee: Stent Tech, Inc, Saint Paul, MN (US)

( * ) Notice: Subject to any disclaimer, the term of this patent is extended or adjusted under 35 U.S.C. 154(b) by 427 days.

(21) Appl. No.: 11/795,737

(22) PCT Filed: Jan. 31, 2006

(86) PCT No.: PCT/US2006/003314
§ 371 (c)(1),
(2), (4) Date: Jan. 27, 2009

(87) PCT Pub. No.: WO2006/083809
PCT Pub. Date: Aug. 10, 2006

(65) Prior Publication Data
US 2009/0132027 A1    May 21, 2009

Related U.S. Application Data

(63) Continuation-in-part of application No. 11/049,323, filed on Feb. 1, 2005, now abandoned.

(51) Int. Cl.
*A61F 2/82* (2006.01)

(52) U.S. Cl. ............... 623/1.35; 623/1.16; 623/1.15

(58) Field of Classification Search ............. 623/1.15, 623/1.35, 1.16
See application file for complete search history.

(56) References Cited

U.S. PATENT DOCUMENTS 5,755,771 A * 5/1998 Penn et al. ............. 623/1.15
2009/0319023 A1 * 12/2009 Hildebrand et al. ......... 623/1.13

FOREIGN PATENT DOCUMENTS

WO    0027307 A1    5/2000

* cited by examiner

*Primary Examiner* — Thomas J Sweet
*Assistant Examiner* — Seema Swaminathan
(74) *Attorney, Agent, or Firm* — Sherrill Law Offices PLLC (57) ABSTRACT

A bifurcated stent 10 and a stent configuration for manufacture of a bifurcated stent 10 are disclosed. The bifurcated stent 10 includes a first mono-tubular stent 12, a second mono-tubular stent 14, and a third mono-tubular stent 16 connected at their proximal ends to form the bifurcated stent 10. The first 12, second 14 and third 16 mono-tubular stents are connected using a first 32, second 34 and third 36 intraconnect extending from the proximal end of the first 12, second 14, and third 16 mono-tubular stents. A reinforcement member 130 may also be provided to reinforce the connection between the intraconnects 32, 34, 36. A reinforcing connector 112, 114, 116 may also be provided.

31 Claims, 7 Drawing Sheets

BIFURCATED STENTING APPRATUS AND METHOD

The application claims the benefit of PCT/US2006/003314 filed on Jan. 31, 2006 which is a CIP of Ser. No. 11/049,323 filed on Feb. 1, 2005.

BACKGROUND OF THE INVENTION

1. Field of the Invention

The present invention relates to medical devices and, more particularly, to bifurcated stents and methods of making bifurcated stents for insertion within branching lumen.

2. Background of the Related Art

Stents and similar implantable medical devices, collectively referred to hereinafter as stents, are generally radially expandable endoprostheses. They are typically used to obtain and maintain the patency of the body passageway while maintaining the integrity of the passageway. Stents have provided doctors with a desirable alternative to the more invasive surgeries historically required to open obstructed passageways within the body. With the tendency being to avoid invasive surgeries, their use and range of applications has steadily increased.

Stents are tubular devices. That is, they comprise a body or wall that defines a lumen. Stents are frequently made of a thin-walled metallic or woven material and have a pattern of apertures, openings or holes defined around the circumference of the stent along most of its length. Typically, the pattern of apertures, openings or holes is configured to permit the stent to move from a contracted to an expanded position. Stents may be constructed from a variety of materials such as stainless steel, Elgiloy, nitinol, shape memory polymers, etc. The materials are typically selected for their biocompatibility among other physical characteristics that may be desirable for particular applications.

Stents are typically configured to be implanted translumenally and enlarged radially after being positioned. They may be implanted in a variety of body lumens or vessels such as within the vascular system, urinary tracts, bile ducts, etc. The stent may provide a prosthetic intralumenal wall or wall support. Some stents are particularly adapted to reinforce blood vessels and to prevent restenosis following angioplasty in the vascular system. In the case of a stenosis, a stent may provide an unobstructed conduit for blood to move through the stenotic region of the vessel. In other variations, a stent may be used to treat an aneurysm by removing the pressure on a weakened part of an artery so as to reduce the risk of embolism, or of the natural artery wall bursting.

Stents may be formed in a variety of methods. For example, a stent may be formed by etching or cutting the stent pattern from a tube or section of stent material; a sheet of stent material maybe cut or etched according to a desired stent pattern whereupon the sheet may be rolled or otherwise formed into the desired tubular or bifurcated tubular shape of the stent; one or more wires or ribbons of stent material may be braided or otherwise formed into a desired shape and pattern.

Stents are typically provided in general two configurations, self-expanding and balloon expandable, or hybrids thereof. Self-expanding stents are generally spring-like devices which are inserted in the body passageway in a contracted state within a catheter or introducer. A self-expanding stent is biased so as to expand upon release from the delivery catheter. When released, the stent reconfigures from a contracted to an expanded position. The self-expanding stent tends to increase to a final diameter dependent on the size and configuration of the stent and the elasticity of the body passageway. Self-expanding stents expand into place when unconstrained, without requiring assistance from a balloon. Balloon expandable stents require mounting over a balloon, positioning, and inflation of the balloon to expand the stent radially outward. Generally, a balloon expandable stent will include a balloon positioned within its central passage. Once the balloon expandable stent has been properly positioned, the balloon is expanded thereby expanding the stent so that the stent is urged in place against the body passageway. As indicated above, the amount of force applied is at least that necessary to maintain the patency of the body passageway. Once properly expanded, the balloon is deflated and withdrawn from the patient. Ideally, the stent will remain in place and maintain the target area of the body passageway substantially open to preserve a desired degree of the passage's function. Some stents may be characterized as hybrid stents which have some characteristics of both self-expandable and balloon expandable stents.

The balloon expandable stent, self-expanding stent, and hybrids thereof may be delivered to the target area of the body passageway by a catheter system. In such systems, the catheter or introducer typically enters the body from an access location outside the body, such as through the patient's skin, or by a "cut down" technique in which the entry blood vessel is exposed by minor surgical means. Accordingly, such systems are typically considered to be minimally invasive. In one exemplary technique, a stent may be implanted in a blood vessel at the site of a stenosis or aneurysm endolumenally. A guide wire is initially passed through the blood vessel to a position near or at the desired point of implantation. A self-expanding stent is typically provided restrained in a radially compressed configuration within a sheath or catheter. A balloon expandable stent typically does not need to be restrained and is therefore merely positioned within a sheath or catheter. The stent and associated catheter are typically configured to be received over the guideware and positioned over the guidewire at the desired location. When the catheter has been properly positioned within the blood vessel, the catheter is manipulated to cause the stent to be removed from the surrounding sheath or catheter in which it is restrained or positioned. The stent then expands or is expanded. Stent expansion may be effected by spring elasticity, balloon expansion, or by the serf-expansion of a thermally or stress-induced return of a memory material to a pre-conditioned expanded configuration. At various points during implantation, various components of the catheter system are withdrawn and typically only the stent remains after implantation.

Recently, small stents have been inserted into coronary arteries after a coronary angioplasty procedure. Coronary angioplasty is a medical procedure used to treat blocked coronary arteries as an alternative to a coronary bypass operation. It involves the insertion of a balloon catheter into the blocked artery and the inflation of the balloon to expand the size of the artery and relieve the blockage. While the procedure is often effective in opening the artery, one problem is the tendency of the artery to reclose in a process known as restenosis. If this occurs, the angioplasty procedure must be repeated which is obviously expensive and may be risky for the patient. The use of a stent after a coronary angioplasty reinforces the walls of the artery and has been shown to prevent reclosing of the artery or to at least prolong the time the artery takes to reclose.

Within the vasculature however, it is not uncommon for stenoses to form at any of a wide variety of vessel bifurcations. A bifurcation is an area of the vasculature or other portion of the body where a first (or parent) vessel is bifurcated into two or more branch vessels. Bifurcations exist within the body in a wide variety of configurations, angles, and vessel diameters. Where a stenotic lesion or lesions form at such a bifurcation, the lesion(s) can affect only one of the vessels (i.e., either of the branch vessels or the parent vessel) two of the vessels, or all three vessels.

Originally, stents shared the common design of being mono-tubular and thus, are best suited to be delivered and implanted in-line in the body passageway. However, mono-tubular stents are not optimal for use at a bifurcation body passageway or about a side branch of a body passageway. When implanted, mono-tubular stents may shield side branches emanating from the target area of the body passageway. In these cases, there is an increased risk of closure of one of the side branches or arm of the bifurcation and, at a minimum, the increased resistance to the movement of fluid through the obscured branch or arm.

To accommodate branching and bifurcations, some techniques have utilized individual stents in each branch of the bifurcated body passageway. However, this approach is fraught with at least two significant problems. First, implantation of three individual stents, together with the expansive forces generated upon implantation results in subjecting the central walls of the bifurcated body passageway to undue stress which may lead to post-procedural complications. Second, since the central walls of the bifurcated body passageway are not supported by the individual stents, this area of the passageway is left substantially unprotected and susceptible to blockage. An array of bifurcated stents have also been developed for application at bifurcations or branches in lumen. However, these stents frequently lack flexibility at the junction of the three branches and are complicated to manufacture.

Thus, there remains a need for a bifurcated stent that may be utilized in a wide variety of vessel bifurcations and branches, without requiring that the stent be extensively modified prior to implantation, and to provide a stent that is capable of supporting the a vessel bifurcation without inhibiting fluid flow.

SUMMARY OF THE INVENTION

This Summary capsulizes some of the claimed aspects of the present invention. Additional details of aspects of the present invention and/or additional embodiments of the present invention are found in the Detailed Description of the Invention. Further, an Abstract of the specification's technical disclosure is included for purposes of complying with 37 C.F.R. 1.72. The Abstract is not intended for use in interpreting the scope of the claims.

In one aspect, the present invention provides a bifurcated stent apparatus. The bifurcated stent apparatus may include a first mono-tubular stent, a second mono-tubular stent and a third mono-tubular stent. The first mono-tubular stent including at least a pair of first intraconnects secured to a proximal end of the first mono-tubular stent. The second mono-tubular stent including at least a pair of second intraconnects secured to a proximal end of the second mono-tubular stent. The third mono-tubular stent including at least a pair of third intraconnects secured to a proximal end of the third mono-tubular stent. The first mono-tubular stent may have a pair of first intraconnects positioned on diametrically opposing sides of the first mono-tubular stent. The second mono-tubular stent may have a pair of second intraconnects positioned on diametrically opposing sides of the second mono-tubular stent. The third mono-tubular stent may have a pair of third intraconnects positioned on diametrically opposing sides of the third mono-tubular stent. Each of the second pair of intraconnects may be secured to one of the first pair of intraconnects of the first mono-tubular stent and each of the third pair of intraconnects may be secured to one of the second pair of intraconnects of the second mono-tubular stent. The first intraconnects, second intraconnects, and third intraconnects may be secured to one another in a generally radial arrangement to form a junction. The first mono-tubular stent may also include one or more first extended expandable members. The second mono-tubular stent may also include one or more second extended expandable members. The third mono-tubular stent may also include one or more third extended expandable members.

In another aspect, the bifurcated stent apparatus may include one or more reinforcing members. The first mono-tubular stent may include one or more first reinforcing connectors secured to the proximal end of the first mono-tubular stent. The second mono-tubular stent may include one or more second reinforcing connectors secured to the proximal end of the second mono-tubular stent. The third mono-tubular stent may include one or more third reinforcing connectors secured to the proximal end of the third mono-tubular stent.

In yet another aspect, the first flexible intraconnect may include a first terminal connector secured to a first flexible connector with the first flexible connector secured to the proximal end of the first mono-tubular stent. The second flexible intraconnect may include a second terminal connector secured to a second flexible connector with the second flexible connector secured to the proximal end of the second mono-tubular stent. The third flexible intraconnect may include a third terminal connector secured to a third flexible connector with the third flexible connector secured to the proximal end of the third mono-tubular stent. A reinforcing member may be secured over two or more of the first terminal connector, the second terminal connector and the third terminal connector to reinforce their connection. At least one of the first terminal connector, the second terminal connector and the third terminal connector may include a first surface and a second surface to secure to an adjacent terminal connector. At least one of the first terminal connector, the second terminal connector and the third terminal connector may bifurcate into a first arm and a second arm with the first arm defining the first surface and with the second arm defining the second surface with each of the first surface and the second surface configured to be secured to an adjacent terminal connector. At least one of the first flexible connector, the second flexible connector and the third flexible connector may comprise an elongated curved member.

In still another aspect, the present invention provides a stent apparatus that includes a stent and a pair of intraconnects secured to a proximal end of the stent. The stent may include one or more extended expandable members. The pair of intraconnects may extend from the proximal end of the stent in an orientation substantially parallel to the longitudinal axis of the stent. The pair of intraconnects may further be positioned on diametrically opposing sides of the proximal end of the stent. The intraconnects may include a terminal connector secured to a flexible connector. The terminal connector may include a first surface and a second surface. The terminal connector may also bifurcate into a first arm and a second arm with the first arm defining a first surface and with the second arm defining a second surface. The flexible connector may be secured to the proximal end of the stent. The flexible connector may be configured as an elongated curved member. One or more reinforcing connectors may also be secured to the proximal end of the stent.

DETAILED DESCRIPTION OF THE INVENTION

Embodiments and components of a bifurcated expandable stent 10 in accordance with the present invention are generally illustrated throughout the figures. The invention is generally described with reference to the figures wherein the same numbers indicate similar, identical or analogous elements in different figures and within individual figures. The elements identified in the figures may be drawn out of the proper proportions for particular applications. However, these proportions have been selected for ease of illustration of the particular elements. Further, the figures are intended to be illustrative rather than limiting and are included to facilitate the explanation of the apparatus of the present invention not to limit the scope of the claims.

A bifurcated stent 10 in accordance with the present invention is generally configured for implantation within the lumen of an animal, such as for example a human. The bifurcated stent 10 may be particularly configured for implantation in a blood vessel. In one aspect, the bifurcated stent 10 may be adapted to maintain the lumen of a blood vessel in an open configuration. In one aspect, the bifurcated stent 10 may be designed for use in a coronary angioplasty. Although the specification may describe aspects of the various embodiments configured for use in coronary angioplasties to simplify the description, those skilled in the art will recognize a variety of applications for a bifurcated stent 10 upon review of this disclosure and will understand how to adapt the disclosed embodiments for these applications.

Figure 1:
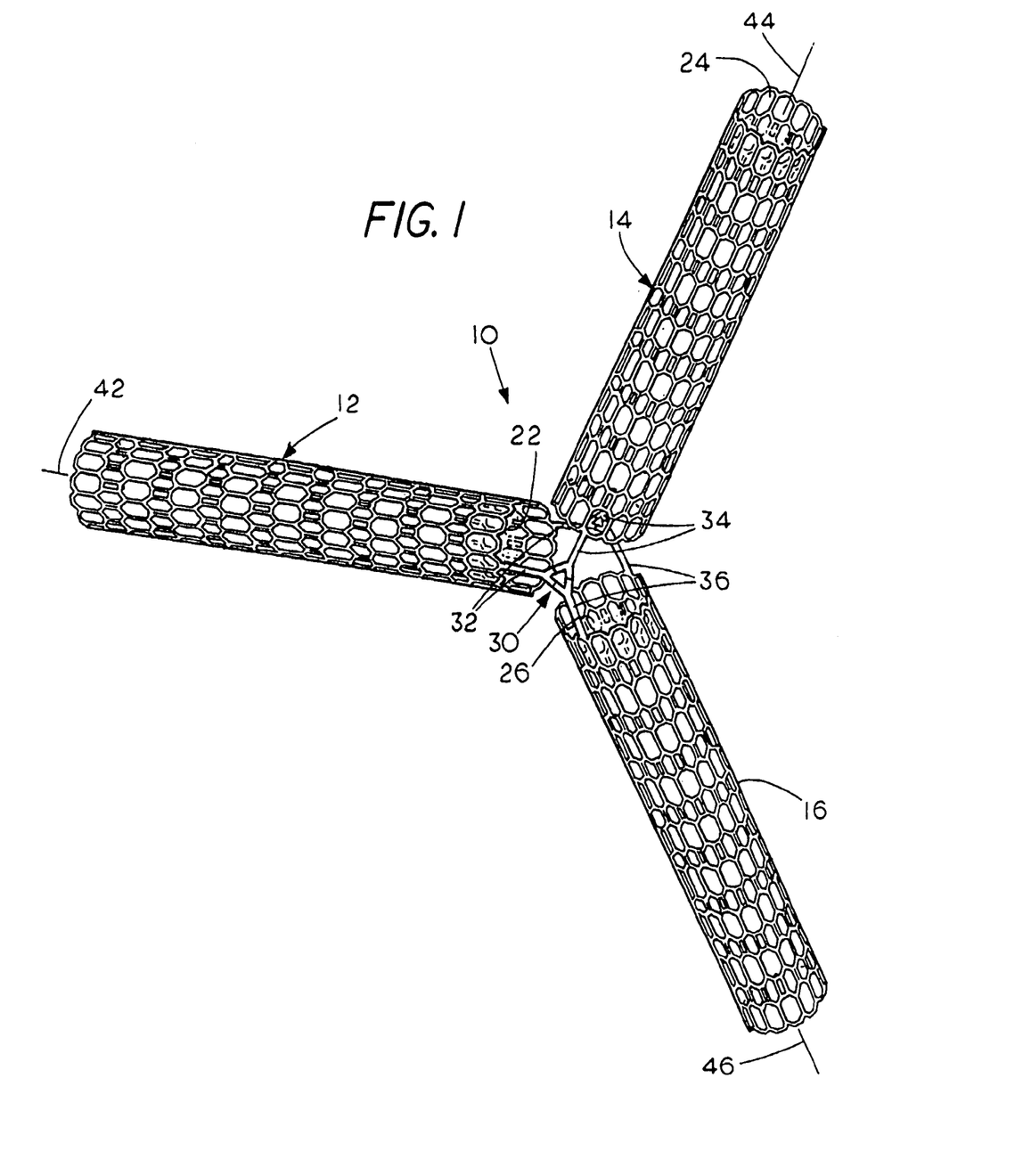
FIG. 1 illustrates a perspective view of an embodiment of a bifurcated stent in accordance with the present invention in an expanded configuration.

FIG. 1 illustrates a bifurcated stent 10 in accordance with the present invention in a radially expanded configuration. As illustrated for exemplary purposes, the bifurcated stent 10 generally includes a first mono-tubular stent 12, a second mono-tubular stent 14, and a third mono-tubular stent 16 joined to one another at a junction 30 by first intraconnect 32, second intraconnect 34 and third intraconnect 36 in a generally radial arrangement. Each of the mono-tubular stents 12, 14, 16 defines a passage 22, 24, 26. The first mono-tubular stent 12 defines a first passage 22; the second mono-tubular stent 14 defines a second passage 24; and the third mono-tubular stent 16 defines a third passage 26. For exemplary purposes, each of the mono-tubular stents 12, 14, 16 may have a wall thickness between the inner surface defining the passage and the exterior surface of about 0.004 inches and may have a diameter of between about 0.030 and 0.080, among other sizes and thicknesses, for certain coronary angioplasty applications as will be recognized by those skilled in the art upon review of the present disclosure.

The passages 22, 24, 26 generally extend between the proximal ends and distal ends and generally in a direction along the longitudinal axis 42, 44, 46 of the respective mono-tubular stents 12, 14, 16. The longitudinal axis 42, 44, 46 have been illustrated as relatively positioned at 120 degree intervals about junction 30 for exemplary purposes. Those skilled in the art will recognize that a variety of spacing may be advantageous for various applications. For example, the longitudinal axis 42 of first mono-tubular stent 12 may be positioned at a 180 degree angle from the longitudinal axis 44 of the second mono-tubular stent 14. In addition, the three mono-tubular stents are illustrated as being substantially co-planar. Those skilled in the art will recognize that a bifurcated stent 10 may be configured with a mono-tubular stent 12, 14, 16 directed outside the plane defined by the other two mono-tubular stents 12, 14, 16 without departing from the scope of the present invention. Further, those skilled in the art will understand that one or more of the mono-tubular stents 12, 14, 16 may include one or more curves along its longitudinal axis which may have advantages in particular applications. Further as illustrated, the mono-tubular stents 12, 14, 16 are generally equivalent in size and general configuration only for exemplary purposes. Those skilled in the art will recognize varying the diameter, length, cell patterns, or general configuration may have advantages in particular applications. For example, the length and diameter for each of the stents may be optimized for both deliverability of the stent and vessel coverage for particular applications.

The bifurcated stent 10 may be manufactured by assembling three independently fabricated mono-tubular stents 12, 14, 16. The similarity of each mono-tubular stent 12, 14, 16 may permit them to be constructed using similar tooling. In addition, the manufacturing of a bifurcated stent 10 from three mono-tubular stents 12, 14, 16 can allow the use of standard stent manufacturing techniques and reduces the need for special or complex tooling typically required for bifurcated systems.

Each of the stents 12, 14, 16 further includes one or more intraconnects 32, 34, 36 at their proximal ends. As illustrated, each of the stents 12, 14, 16 includes a pair of intraconnects 32, 34, 36 at their proximal ends for exemplary purposes. For purposes of describing the elements and construction of the bifurcated stent 10, the term proximal shall refer to the end of the components adjacent to junction 30 and the term distal shall refer to the end opposite the proximal end of each element. The first stent 12 includes a first flexible intraconnect 32, the second stent 14 includes a second flexible intraconnect 34, and the third stent 16 includes a third flexible intraconnect 36. The intraconnects 32, 34, 36 are used to secure each of the stents 12, 14, 16 relative to one another to form a bifurcated stent 10. Intraconnects 32, 34, 36 are configured to be secured at their distal ends to the proximal ends of the stents 12, 14, 16 and at their proximal ends to one another. Typically, the intraconnects 32, 34, 36 are secured to one another by laser welding. However, the intraconnects 32, 34, 36 may be welded using alternative methods, adhesively bonded or otherwise secured to one another as will be understood by those skilled in the art upon review of the present disclosure. In one aspect, the intraconnects 32, 34, 36 may function to maintain the distal openings for each of the passages of each of the stents in a position adjacent to one another, as illustrated in FIG. 1. In another aspect, the intraconnects 32, 34, 36 may function to provide a flexible junction between the three stents. This flexible junction may permit a wide variation in the relative angles of the implanted stents without the kinking and associated obstruction of the passages junction that may be associated with stents having an expandable cell structure at their junction.

A bifurcated stent 10 may include any number of configurations to facilitate expandability. Typically, stents are typically configured with a pattern of cells designed to optimize the characteristics of radial expansion and strength, among other characteristics, as appropriate for particular applications. The bifurcated stent 10 may include an open cell or a closed cell configuration to facilitate expansion in the radial direction. The open cell configurations may include any number of radially expandable windings connected by interconnects as will be recognized by those skilled in the art. The closed cell designs may include a variety of triangular, pentagonal, hexagonal, diamond and other shaped cells as well as a variety of irregular shaped cells or combinations thereof that will be recognized by those skilled in the art. The cells are frequently formed as regular or repeating patterns. Some exemplary open and closed cell configurations are disclosed in U.S. Patent Application Publication no. 2002/0133222 the disclosure of which is hereby incorporated by reference. However, the construction of a bifurcated stent 10 is not particularly limited to any particular design, architecture, fabrication method, deployment method, or materials.

A bifurcated stent 10 may be formed from a range of materials including polymers and metals. The polymers can include a wide range of materials including shape memory polymers. Typically metals are selected from stainless steel, Elgiloy, nitinol, gold, platinum, tantalum, silver and among other metals or combinations thereof. In one aspect, type 316 stainless steel may be used such as type 316 L or 316 Lvm. These stainless steels are generally selected for their low carbon content which is typically considered beneficial in many manufacturing processes, such as for example, to reduce the brittleness of weld joints. Typically, the material is selected for their physical characteristics as well as their biocompatibility. Desirable characteristics of the material typically include deformability and the ability to hold the shape once deformed. It may also be desirable that the stents include some radiopaque materials. Stents made of stainless steel which have a thickness of 0.005 inch are generally radiopaque, however, stents having lesser thicknesses, such as stents made specifically for use in coronary arteries which often requires thicknesses less than 0.005 inch (often for example about 0.003 inch) need to be coated with a radiopaque material such as 24 carat gold to a thickness of about 0.0002 inch. In addition, other coatings including specific functional agents may also be employed to address issues such as blood clotting or reduction in the amount of intimal hyperplasia and resulting restenosis. Methods to coat metal prostheses to make them radiopaque or to minimize the risks due to blood clotting are known to those skilled in the art.

Figure 2:
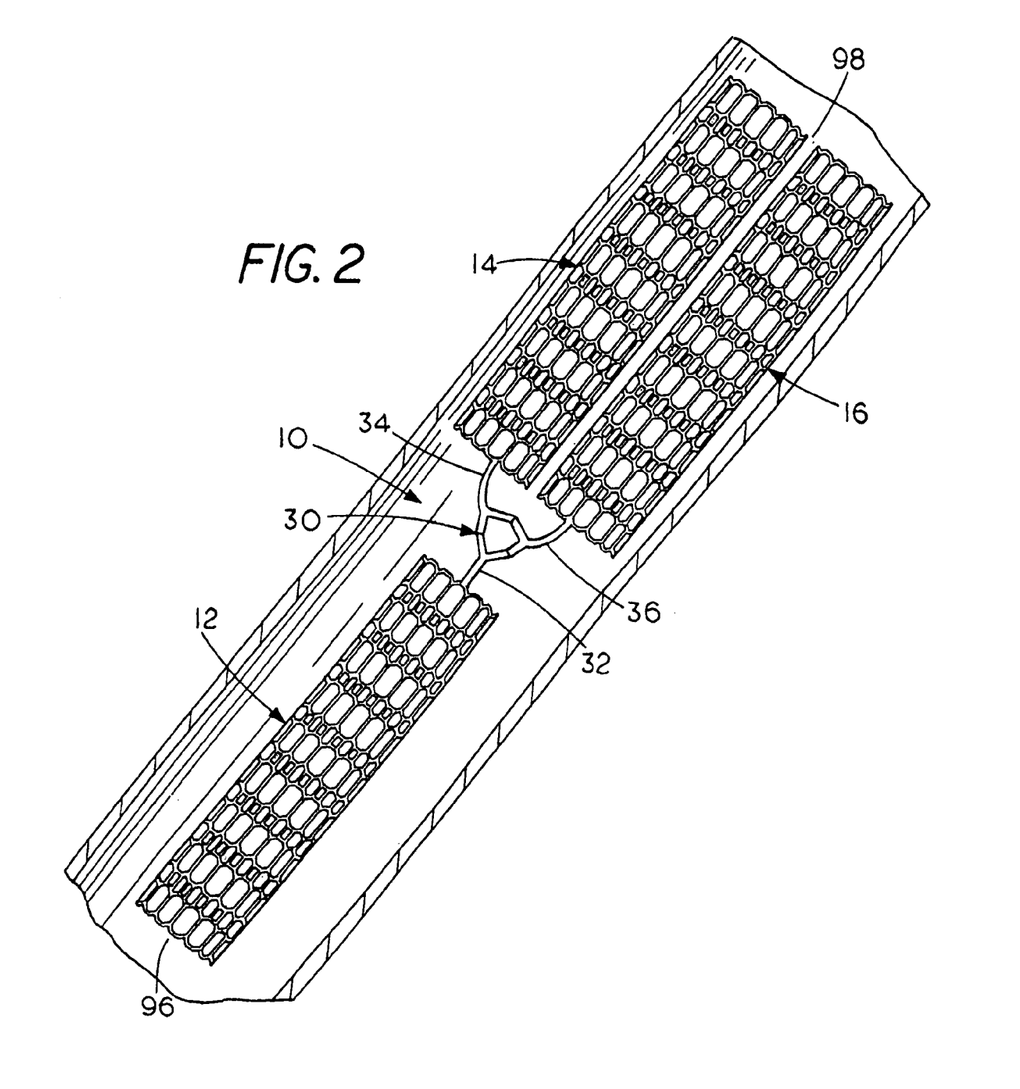
FIG. 2 illustrates a side view of the embodiment of the bifurcated stent depicted in FIG. 1 in an unexpanded configuration.

Another embodiment of a bifurcated stent 10 is generally illustrated in the collapsed position within a vessel in FIG. 2. For ease of description of the bifurcated stent's 10 implantation, the collapsed and folded bifurcated stent 10 may have its ends labeled as proximal end 96 and distal end 98 as illustrated in FIG. 2. A bifurcated stent 10 in the collapsed and folded position has a smaller profile than in its expanded position to permit the bifurcated stent 10 to be positioned coaxially within a lumen in a human patient or animal. Generally as used herein, the term "profile" refers to the largest width of any portion of the bifurcated stent 10 in a collapsed and folded (as illustrated in FIG. 2) configuration. When in the folded position, the first mono-tubular stent 12 may extend along substantially the same longitudinal axis although in the opposite direction as second mono-tubular stent 14 and third monotubular stent 16 for exemplary purposes. As illustrated, the bifurcated stent 10 is collapsed and folded to permit its insertion within the lumen of the illustrated catheter or introducer. This use of proximal end 96 and distal end 98 herein shall be limited to discussions of implantation.

A bifurcated stent 10 in accordance with the present invention may be configured as a balloon expandable stent, a self expanding stent or a hybrid thereof. Accordingly, a bifurcated stent 10 in accordance with the present invention may temporarily fitted upon or generally coaxial with a balloon catheter, if configured as a balloon expandable stent. In one aspect, a collapsed bifurcated balloon catheter may be positioned within the collapsed stent including a branch of the balloon catheter extending from the first mono-tubular stent 12 into the second mono-tubular stent 14 and a second branch of the balloon catheter extending from the first mono-tubular stent 12 into the third mono-tubular stent 16.

Figure 3A:
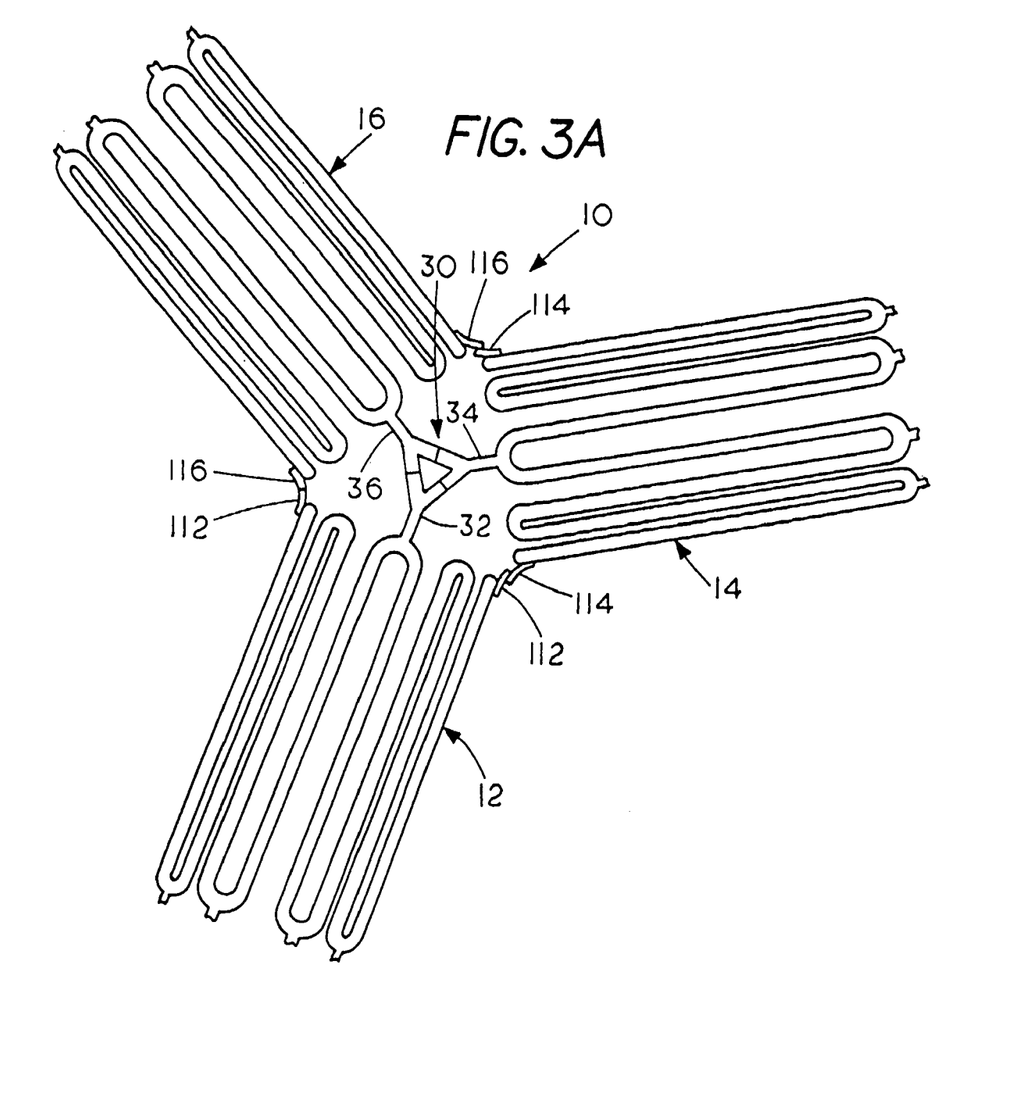
FIG. 3A illustrates a partial side view of an embodiment of a junction of the three expandable tubes of a bifurcated stent in accordance with the present invention.
Figure 3B:
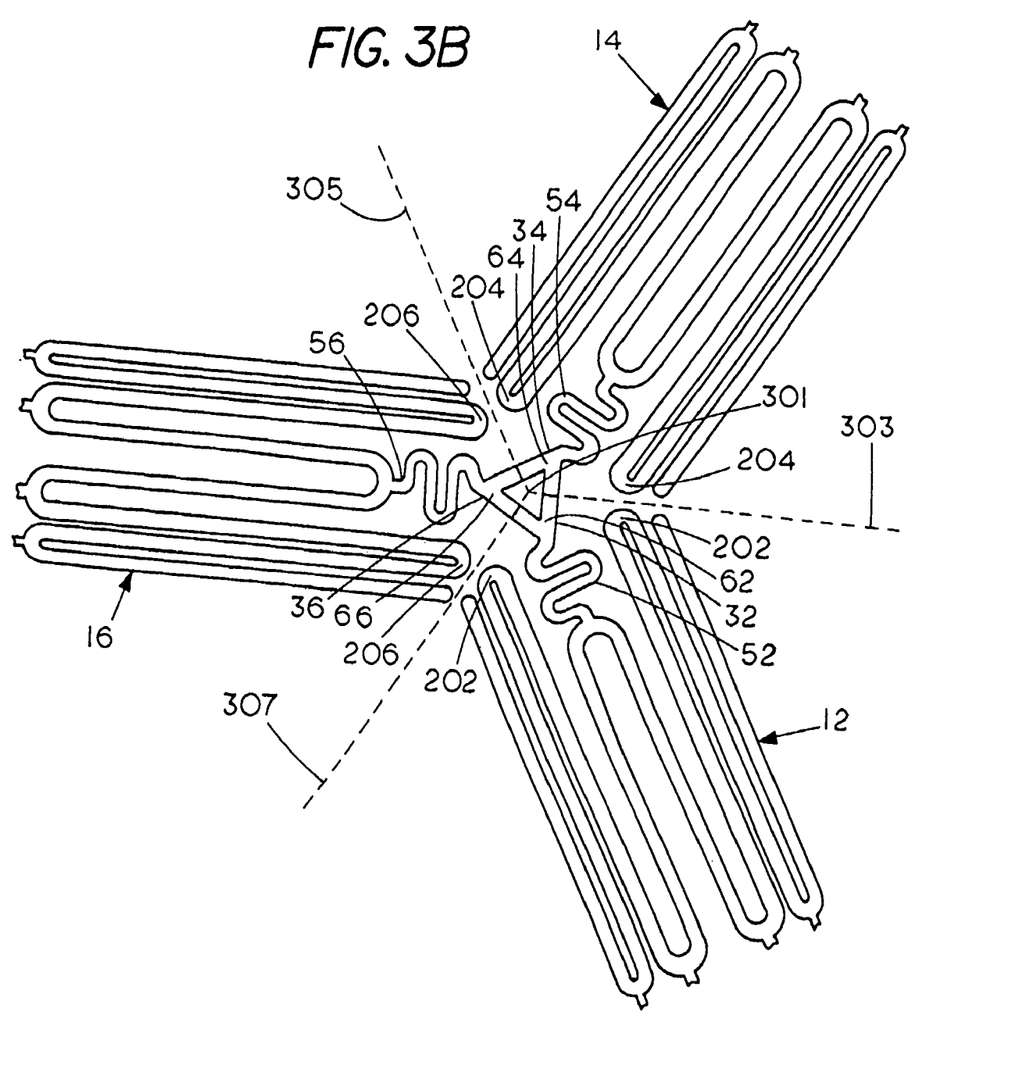
FIG. 3B illustrates a partial side view of another embodiment of a junction of the three expandable tubes of a bifurcated stent in accordance with the present invention.

FIGS. 3A and 3B illustrate details of embodiments of a junction 30 and intraconnects 32, 34, 36 for connecting the three mono-tubular stents 12, 14, 16 into a bifurcated stent 10. Intraconnects 32, 34, 36 may include flexible connectors 52, 54, 56 and terminal connectors 62, 64, 66. The flexible connectors 52, 54, 56 are configured to be secured to the proximal end of a stent 12, 14, 16. In one aspect, the flexible connector 52, 54, 56 may be integrally formed at the proximal end of the mono-tubular stent 12, 14, 16. In other aspects, the flexible connector 52, 54, 56 is secured to the mono-tubular stents 12, 14, 16 such as, for example, by welding or an adhesive. The flexible connectors 52, 54, 56 are typically integral with the terminal connectors 62, 64, 66. However, the flexible connectors 52, 54, 56 may be separately constructed and secured to the flexible connectors 52, 54, 56 as will be understood by those skilled in the art. The terminal connectors 62, 64, 66 are typically positioned at a proximal end of the flexible connectors 52, 54, 56. The terminal connectors 62, 64, 66 of each mono-tubular stent 12, 14, 16 are configured to be secured to one another when the mono-tubular stents 12, 14, 16 are positioned about junction 30. The flexible connectors 52, 54, 56 generally function to relatively position the three mono-tubular stents 12, 14, 16 relative to interconnected the terminal connectors 62, 64, 66 to form a bifurcated stent 10.

The flexible connectors 52, 54, 56 may provide some flexibility in the connection of the three mono-tubular stents 12, 14, 16. As illustrated in FIG. 3B, the flexible connectors 52, 54, 56 may comprise an elongated linear member to position the terminal connectors 62, 64, 66 relative to their respective mono-tubular stents 12, 14, 16. The elongated linear member may be sized and proportioned to provide the desired spacing and other characteristics, including but not limited to flexibility or lack thereof, for particular applications. As illustrated in FIG. 3B, the flexible connectors 52, 54, 56 may comprise an elongated curved member to position the terminal connectors 62, 64, 66 relative to their respective mono-tubular stents 12, 14, 16. As illustrated, the elongated curved member which comprises the flexible connectors 52, 54, 56 of FIG. 3B includes a plurality of bends along its length which may provide desired flexibility characteristics and/or may provide increased surface area to provide more supporting surface for a vessel within a patient. In addition or alternatively, the elongated curved member may provide a greater surface area to enhance drug elution characteristics.

As illustrated, each of the terminal connectors 62, 64, 66 of FIGS. 3A and 3B are of a bifurcated design. The bifurcated design provides a first surface 72, 74, 76 and a second surface 82, 84, 86 to be secured to the adjacent terminal connectors 62, 64, 66. The bifurcated design may also separate the points at which the terminal connectors 62, 64, 66 are secured which can increase the strength of the junction. As illustrated, each of the first surfaces 72, 74, 76 may be welded or otherwise secured to the corresponding second surface 82, 84, 86 of the adjacent terminal connector 62, 64, 66. Accordingly, the three corresponding first surface 72, 74, 76 and second surfaces 82, 84, 86 are interconnected by three welds 102, 104, 106. In the illustrated embodiment, the bifurcated stent 10 would maintain its integrity if any one of the three welds 102, 104, 106 should fail.

FIG. 3B further provides a bifurcated stent 10 having extended expandable members 202, 204, 206 of mono-tubular stents 12, 14, 16, respectively. As illustrated, first mono-tubular stent 12 includes a pair of first extended expandable members 202; second mono-tubular stent 14 includes a pair of second extended expandable members 204; and third mono-tubular stent 12 includes a pair of third extended expandable members 204. Extended expandable members 202, 204, 206 extend into the gaps about junction 30. In one aspect, extended expandable members 202, 204, 206 may function to increase surface area of the bifurcated stent 10. The increased surface area may improve the support and/or drug elution characteristics of the bifurcated stent 10. As illustrated, extended expandable members 202, 204, 206 are portions of mono-tubular stents 12, 14, 16 which extend toward the intersecting planes, 303, 305, 307 which radiate out from the axis 301 extending through and representing the center of the junction 30. For stent 12, each of the extended expandable members 202 extend from the proximal end of the stent 12 to a point approaching the adjacent plane 303, 307. For stent 14, each of the extended expandable members 204 extend from the proximal end of the stent 14 to a point approaching the adjacent plane 303, 305. For stent 16, each of the extended expandable members 206 extend from the proximal end of the stent 16 to a point approaching the adjacent plane 305, 307. Accordingly, the gaps about the junction 30 as illustrated in FIG. 3A may be minimized by the extended expandable members 202, 204, 206 of FIG. 3B.

Figure 4:
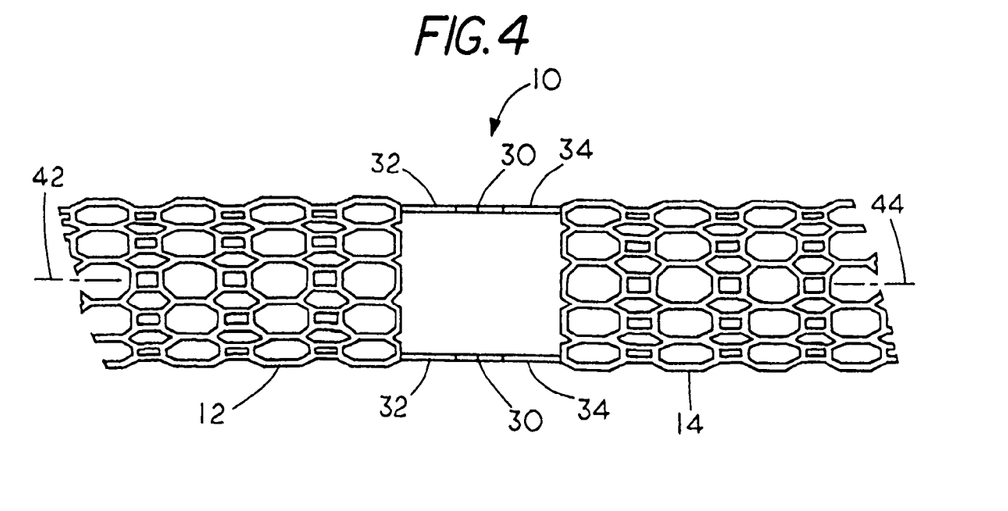
FIG. 4 illustrates a partial top view of an embodiment of a bifurcated stent in accordance the present invention showing details of embodiments of the intraconnects and showing the individual expandable stent portions schematically.

FIG. 4 illustrates a top view of an embodiment of the connection between and relative positioning of two of the three mono-tubular stents 12, 14 of a bifurcated stent 10 for exemplary purposes. FIG. 4 illustrates aspects of the present invention including a pair of first intraconnects 32 and a pair of second intraconnects 34 secured at the proximal ends of first stent 12 and second stent 14, respectively. The intraconnects 32, 34 are positioned on diametrically opposing sides of the respective stents 12, 14 to which they are secured. Alternatively, intraconnects 32, 34 may be otherwise positioned about the periphery of their respective stents 12, 14 to particularly adapt the mechanical characteristics of the bifurcated stent 10 to particular applications. The illustrated intraconnects 32, 34 extend in a direction parallel or substantially parallel to the longitudinal axis 42, 44 of the stent 12, 14 to which they are secured for exemplary purposes. In addition, each pair of intraconnects 32, 34 is illustrated as extending in a direction parallel or substantially parallel to one another. Those skilled in the art will recognize a wide variety of configurations and positioning for intraconnects 32, 34 upon review of the present disclosure.

Figure 5:
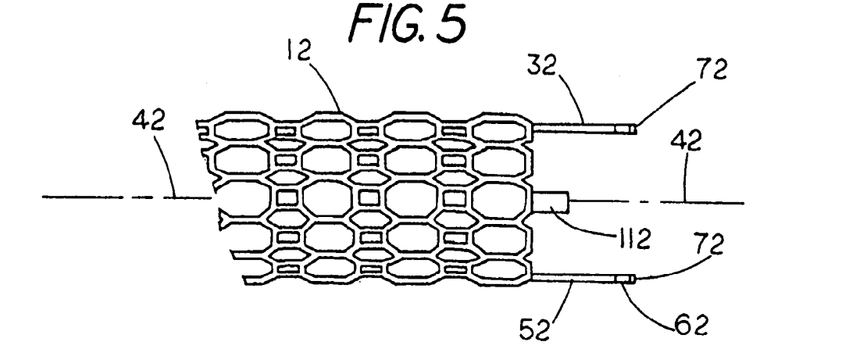
FIG. 5 illustrates a partial top view of an embodiment of an individual expandable stent in accordance with the present invention showing details of embodiments of the intraconnects and reinforcing connectors and showing the expandable stent portion schematically.
Figure 6:
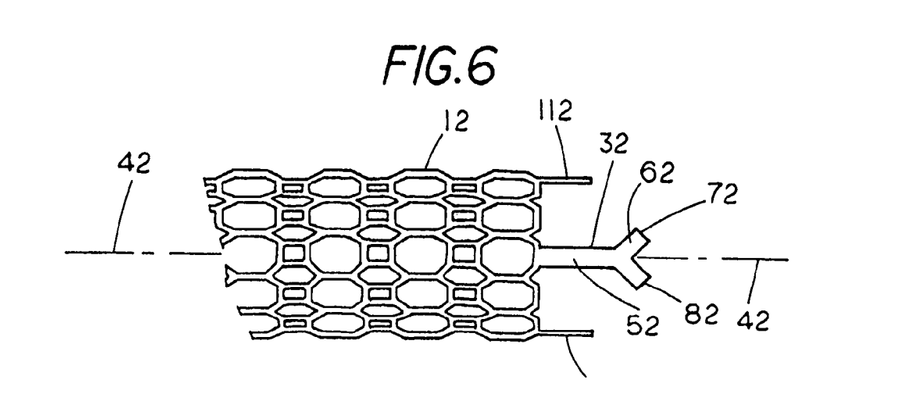
FIG. 6 illustrates a partial side view of an embodiment of an individual expandable stent in accordance with the present invention showing details of embodiments of the intraconnects and reinforcing connectors and showing the expandable stent portion schematically.

FIGS. 5 and 6 illustrate a partial top and a partial side view of the proximal end of a stent 12. FIGS. 5 and 6 illustrate aspects of the present invention including a pair of first intraconnects 32 and a pair of reinforcing connectors 112 secured at the proximal ends of first stent 12. As illustrated, the intraconnects 32 are again positioned on diametrically opposing sides of the stent 12 to which they are secured. The illustrated intraconnects 32 also again extend in a direction parallel or substantially parallel to the longitudinal axis 42 of the stent 12. In addition, the pair of intraconnects 32 is illustrated as extending in a direction parallel or substantially parallel to one another. The embodiments of FIG. 3A also include the illustrated a pair of reinforcing connectors 112, 114, 116. As illustrated, first mono-tubular stent 12 includes a pair of first reinforcing connectors 112, second mono-tubular stent 14 includes a pair of second reinforcing connectors 114, and third mono-tubular stent 14 includes a pair of third reinforcing connectors 116. Reinforcing connectors 112, 114, 116 are configured to be secured to either the body of an adjacent stent 12, 14, 16 of the bifurcated stent 10 or to an adjacent reinforcing connector 112, 114, 116 on an adjacent stent 12, 14, 16 of the bifurcated stent 10 as illustrated in FIG. 3A. The reinforcing connectors 112, 114, 116 are typically secured to the proximal end of a stent. In one aspect, the reinforcing connectors 112, 114, 116 may be integrally formed at the proximal end of the stent. In other aspects, the reinforcing connectors 112, 114, 116 may be secured to the stent such as, for example, by welding or an adhesive. The configuration of the reinforcing connector 112, 114, 116 as well as their point of attachment can affect the configuration and characteristics of the resulting bifurcated stent. As illustrated in FIGS. 5 and 6 for exemplary purposes, the pair of reinforcing connectors 112 is positioned on diametrically opposing sides of the stent 12 to which they are secured. As illustrated, the reinforcing connectors 112 extend in a direction parallel or substantially parallel to the longitudinal axis 42 of the stent 12. In addition, the pair of reinforcing connectors 112 is illustrated as extending in a direction parallel or substantially parallel to one another.

Figure 7A:
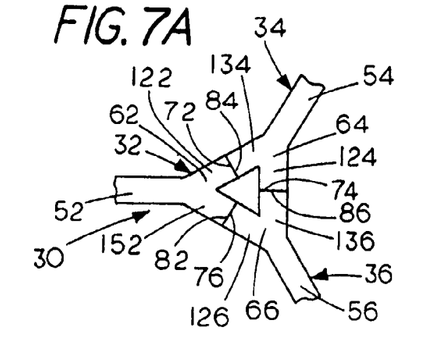
FIG. 7A illustrates a detailed partial side view of embodiments of intraconnects secured to one another in accordance with the present invention.
Figure 7B:
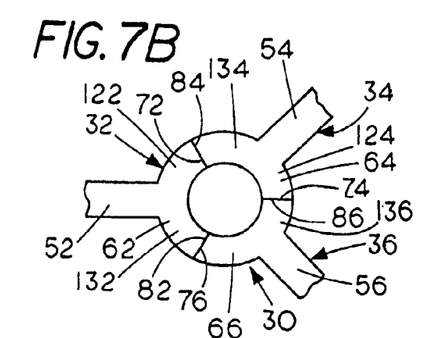
FIG. 7B illustrates a detailed partial side view of embodiments of intraconnects secured to one another in accordance with the present invention.
Figure 7C:
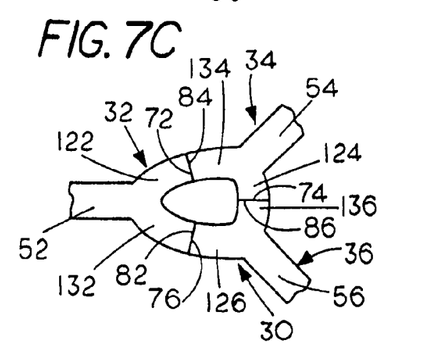
FIG. 7C illustrates a detailed partial side view of embodiments of intraconnects secured to one another in accordance with the present invention.
Figure 7D:
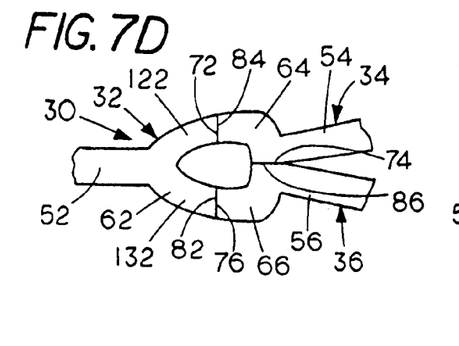
FIG. 7D illustrates a detailed partial side view of embodiments of intraconnects secured to one another in accordance with the present invention.
Figure 7E:
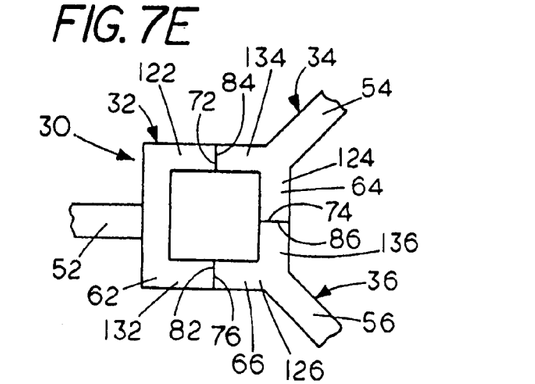
FIG. 7E illustrates a detailed partial side view of embodiments of intraconnects secured to one another in accordance with the present invention.

FIGS. 7A to 7E illustrate exemplary embodiments of terminal connectors 62, 64, 66 of intraconnects 32, 34, 36 having bifurcations and their interconnection at junction 30. Each of the figures only provides a partial illustration of the flexible connectors 52, 54, 56. Again as illustrated, each of the first surfaces 72, 74, 76 may be welded or otherwise secured to the corresponding second surface 82, 84, 86 of the adjacent terminal connector 62, 64, 66. As illustrated in FIGS. 7A to 7E each of the intraconnects 32, 34, 36 includes a bifurcated terminal connector 62, 64, 66. The bifurcated terminal connectors 62, 64, 66 bifurcate into first arms 122, 124, 126 and second arms 132, 134, 136. The first arms 122, 124, 126 include the first surfaces 72, 74, 76. The second arms 132, 134, 136 include the second surfaces 82, 84, 86. As illustrated in FIGS. 7A and 7B, the first arms 122, 124, 126 and second arms 132, 134, 136 of the adjacent terminal connectors 62, 64, 66 may be similarly shaped and symmetrically disposed about junction 30. As illustrated in FIGS. 7C to 7E, the first arms 122, 124, 126 and second arms 132, 134, 136 of each terminal connector 62, 64, 66 may vary in shape and have a varying symmetry. In one aspect, each of the embodiments of FIGS. 7A to 7E illustrates embodiments spatially separating the first surface 72, 74, 76 from the second surface 82, 84, 86.

Figure 8A:
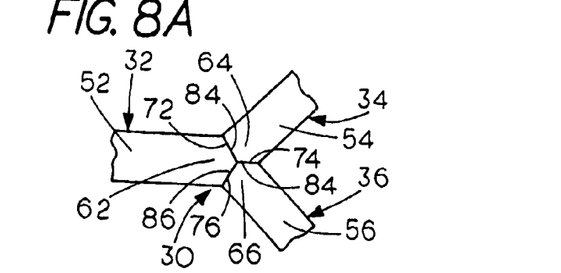
FIG. 8A illustrates a detailed partial side view of embodiments of intraconnects secured to one another in accordance with the present invention.
Figure 8B:
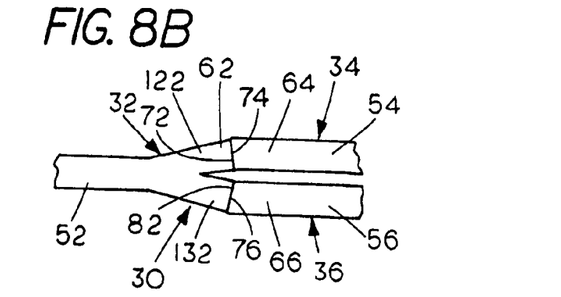
FIG. 8B illustrates a detailed partial side view of embodiments of intraconnects secured to one another in accordance with the present invention.
Figure 8C:
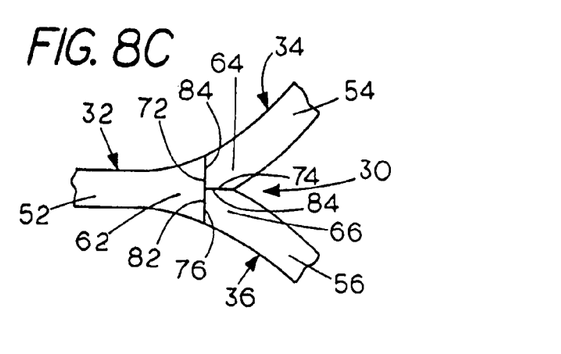
FIG. 8C illustrates a detailed partial side view of embodiments of intraconnects secured to one another in accordance with the present invention.

FIGS. 8A to 8C illustrate exemplary embodiments of terminal connectors 62, 64, 66 of intraconnects 32, 34, 36 alternative configurations and their interconnection at junction 30. Each of the figures only provides a partial illustration of the flexible connectors 52, 54, 56. As illustrated in FIG. 8A, the first arms 122, 124, 126 and second arms 132, 134, 136 of the adjacent terminal connectors 62, 64, 66 may be similarly shaped and symmetrically disposed about junction 30. As illustrated in FIGS. 8B to 8C, the first arms 122, 124, 126 and second arms 132, 134, 136 of each terminal connector 62, 64, 66 may vary in shape and have a varying symmetry.

As illustrated in FIGS. 8A and 8C, each of the terminal connectors 62, 64, 66 includes a first surfaces 72, 74, 76 and a second surface 82, 84, 86. The first surfaces 72, 74, 76 may be welded or otherwise secured to the corresponding second surface 82, 84, 86 of the adjacent terminal connector 62, 64, 66.

As illustrated in FIG. 8B only the flexible interconnect 32 includes a bifurcated terminal connector 62. Accordingly only the flexible interconnect 32 defines a first arm including the first surface and a second arm including a second surface. The terminal connectors 64, 66 of the embodiment of FIG. 8B are not bifurcated therefore include only a first surface 74, 76. The first surface 74 of terminal connector 64 is secured to the second surface 82 of terminal connector 62 and the first surface 76 of terminal connector 66 is secured to the first surface 72 of terminal connector 62.

Figure 9:
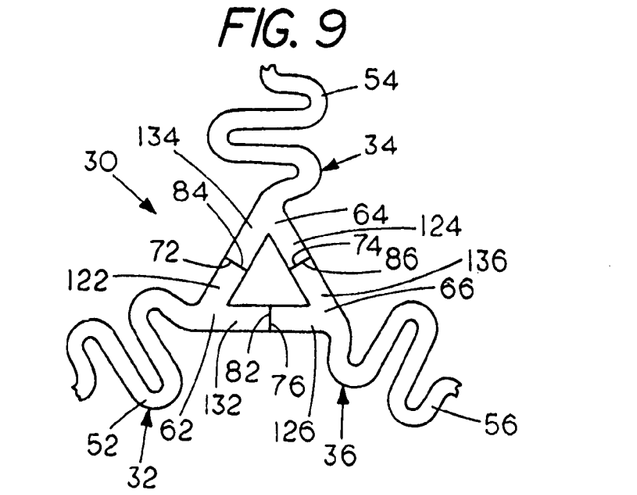
FIG. 9 illustrates a detailed partial side view of embodiments of intraconnects secured to one another in accordance with the present invention.

FIG. 9 illustrates another exemplary embodiment of the flexible connectors 52, 54, 56 of intraconnects 32, 34, 36 comprising elongated curved members to position the terminal connectors 62, 64, 66 relative to their respective mono-tubular stents 12, 14, 16. As illustrated, the elongated curved members which comprise the flexible connectors 52, 54, 56 of FIG. 9 include a plurality of bends along their length which may provide desired flexibility characteristics and/or may provide increased surface area to provide more supporting surface for a vessel within a patient. In addition or alternatively, the elongated curved member may provide a greater surface area to enhance drug elution characteristics. Again as illustrated, each of the first surfaces 72, 74, 76 may be welded or otherwise secured to the corresponding second surface 82, 84, 86 of the adjacent terminal connector 62, 64, 66. As illustrated in FIG. 9, each of the intraconnects 32, 34, 36 includes a bifurcated terminal connector 62, 64, 66. The bifurcated terminal connectors 62, 64, 66 bifurcate into first arms 122, 124, 126 and second arms 132, 134, 136. The first arms 122, 124, 126 include the first surfaces 72, 74, 76. The second arms 132, 134, 136 include the second surfaces 82, 84, 86. As illustrated in FIG. 9, the first arms 122, 124, 126 and second arms 132, 134, 136 of the adjacent terminal connectors 62, 64, 66 may be similarly shaped and symmetrically disposed about junction 30. As illustrated in FIG. 9, the first arms 122, 124, 126 and second arms 132, 134, 136 of each terminal connector 62, 64, 66 may vary in shape and have a varying symmetry. In one aspect, each of the embodiment of FIG. 9 illustrates embodiments spatially separating the first surface 72, 74, 76 from the second surface 82, 84, 86.

Figure 10A:
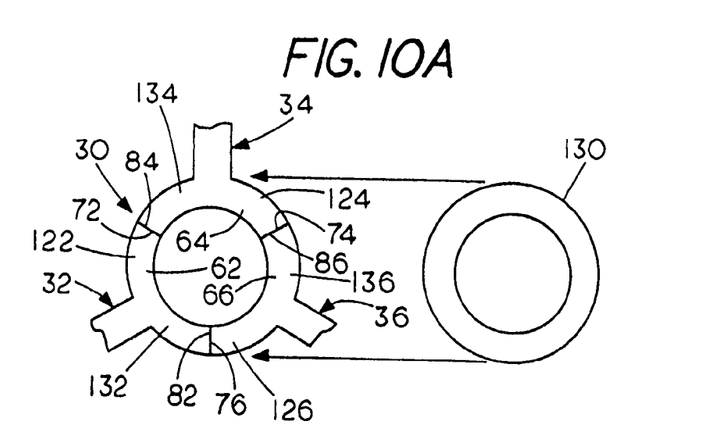
FIG. 10A illustrates a partial top view of an embodiment of the positioning of a reinforcing member over a junction.
Figure 10B:
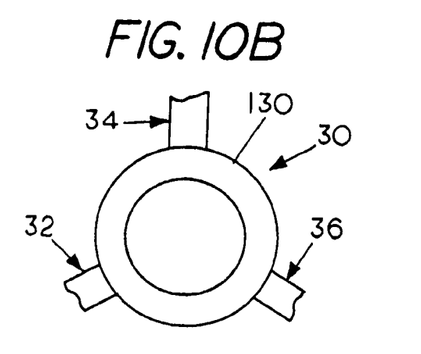
FIG. 10B illustrates a partial top view of an embodiment of a reinforcing member secured to a junction.
Figure 10C:
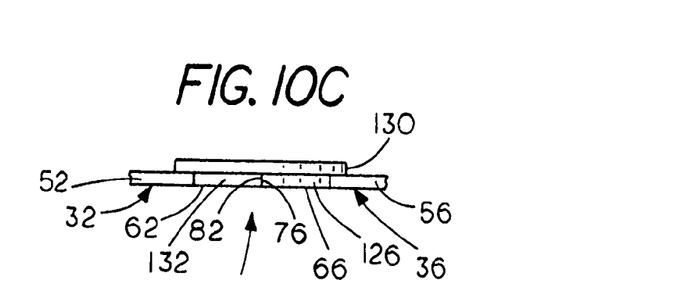
FIG. 10C illustrates a partial side view of an embodiment of a reinforcing member secured to a junction.

FIGS. 10A, 10B and 10C illustrate an exemplary embodiment of terminal connectors 62, 64, 66 of intraconnects 32, 34, 36 having an embodiment of a reinforcement member 130 secured to a surface of the terminal connectors 62, 64, 66. FIGS. 10A, 10B and 10C illustrate an exemplary embodiment of terminal connectors 62, 64, 66 having bifurcations and their interconnection at junction 30. Again as illustrated, each of the first surfaces 72, 74, 76 may be welded or otherwise secured to the corresponding second surface 82, 84, 86 of the adjacent terminal connector 62, 64, 66. As illustrated in FIGS. 10A, 10B and 10C each of the intraconnects 32, 34, 36 includes a bifurcated terminal connector 62, 64, 66. With the illustrated embodiment, the terminal connectors 62, 64, 66 substantially form a circle or ring when secured together. In one aspect, a reinforcement member 130 may be secured to a surface of the terminal connectors 62, 64, 66 to reinforce one or more of the junctions between the terminal connectors 62, 64, 66. As illustrated for exemplary purposes the reinforcement member 130 is coextensive with the entirety of a surface of each of the terminal connectors 62, 64, 66. In another aspect, the reinforcement member 130 may span only a single junction between adjacent terminal connectors 62, 64, 66. In yet another aspect, a plurality of reinforcement members 130 may be provided with each reinforcement member spanning a single junction between adjacent terminal connectors 62, 64, 66.

Manufacture

Each mono-tubular stent 12, 14, 16 of a bifurcated stent 10 in accordance with the present invention may be manufactured using a range of techniques known to those skilled in the art. Generally, the each mono-tubular stent 12, 14, 16 may be made by laser cutting, water-jet cutting, or chemical etching of a preformed tube or a sheet to be rolled into a tube; by molding; by weaving; or by other methods that will be recognized by those skilled in the art upon review of the present disclosure. In one exemplary method, the mono-tubular stent 12, 14, 16 can be cut from a tube. In this method, the mono-tubular stent 12, 14, 16 is generally formed by removal of material from the cylindrical wall of the tube. The material remaining typically forms the mono-tubular stent 12, 14, 16. An exemplary apparatus and method for manufacturing mono-tubular stents 12, 14, 16 in accordance with the present invention are disclosed in U.S. Pat. Nos. 5,852,277 and 6,114,653, the disclosures of which are hereby incorporated by reference. After cutting, the cut mono-tubular stent 12, 14, 16 is typically cleaned to remove the laser scale. This cleaning may be accomplished using chemicals and methods that are known to those skilled in the art. The mono-tubular stent 12, 14, 16 may then be heat treated in an annealing process to 1850 degrees Fahrenheit followed by cooling with nitrogen to a temperature of about 100 degrees Fahrenheit before removing from the furnace. A number of branches are then laser welded to form a mono-tubular stent 12, 14, 16 in accordance with the present invention. Typically, three mono-tubular stents 12, 14, 16 are welded together to form a bifurcated stent 10 in accordance with the present invention. An exemplary apparatus and method for welding the components of a bifurcated stent 10 in accordance with the present invention are disclosed in U.S. Pat. No. 5,324,913 the disclosure of which is hereby incorporated by reference. In one aspect, the three mono-tubular stent 12, 14, 16 may be laser welded together. When laser welded, each of the three mono-tubular stent 12, 14, 16 may be fitted over an individual mandrel. The ends of the mandrels may then be secured in a radial orientation a single point and the mono-tubular stent 12, 14, 16 may then be positioned on the mandrel such that the terminal connectors 62, 64, 66 are properly positioned relative to one another for laser welding. The terminal connectors 62, 64, 66 may then be laser welded at their first surfaces 72, 74, 76 and/or second surfaces 82, 84, 86. The mandrels may then be removed to leave the substantially completed bifurcated stent 10.

Implantation

The bifurcated stent 10 of the present invention may be introduced by any known surgical procedure. In one aspect, the device is introduced endoluminally over a pair of guidewires. Initially, a pair of guidewires is inserted into a vessel and are fed through the vessel to the target location. At the target location, the first guidewire is inserted into a first branch of the vessel and the second guidewire inserted into a second branch of the vessel. The manner by which the guidewires are inserted is conventional and within the purview of a person skilled in the art. The guidewires are then threaded through the stent. With the stent in a collapsed position, the first guidewire is inserted through a first arm of the stent and the second guidewire is inserted through the second arm of the stent. The stent is then directed to the target location over the guidewires and usually in association with a catheter or n antroducer to the target location. The location of the stent within a patient may be identified by fluoroscopy using radiopaque markers. The individual arms of the stent should follow their respective guidewires into the proper branch of the vessel. Once the first arm of the stent has been directed into the first branch of the vessel and the second arm of the stent has been properly positioned in the second branch of the vessel, the guidewire may be removed and the stent may be expanded. The deployed device may be further inspected using fluoroscopy to insure that it is properly positioned. Regardless of how the stent is initially deployed, balloon devices may be used to model the members into place to conform to the topography of the lumen, as will be understood by those skilled in the art upon review of the present disclosure.

A number of methods may be utilized for the expansion of the bifurcated stent 10. For example, a pair of balloon catheters may be used to expand the bifurcated stent 10 with one of the balloons extending into the first branch and the other balloon extending into the second stent. Alternatively, a single bifurcated balloon catheter design which corresponds to the design of the stent may be used with the first of the balloons bifurcations extending into the first branch and the second of the balloon catheters bifurcations extending into a second branch. Alternatively, the bifurcated stent 10 could be composed of a material designed to expand when passageways 22, 24, 26 are flushed with a liquid having an elevated temperature. Typically, the temperatures are elevated to around 150 to 160 degrees Fahrenheit. In another can be designed as self-expanding to be implanted as described above. In this embodiment, the radially outward force exerted on the stent would be generated within the stent itself. Other methods for stent expansion may be apparent to those skilled in the art upon review of the present disclosure.

Furthermore, although illustrated and described herein with reference to certain specific embodiments, the present invention is nevertheless not intended to be limited to the details provided in the foregoing description. Rather, various modifications may be made in the details within the scope and range of equivalents of the claims and without departing from the spirit of the invention.

What is claimed is:

1. A mono-tubular stent for assembly into a bifurcated stent,
    said mono-tubular stent having a pair of interconnects secured to a proximal end thereof,
    said intraconnects extending from the proximal end of the stent in an orientation substantially parallel to the longitudinal axis of the stent,
    the intraconnects defining a first surface and a second surface the first surface configured such that the first surface of the intraconnect meets to join endlessly together and form a flexible junction to secure the one mono-tubular stent to another mono-tubular stent and the second surface configured such that the second surface of the intraconnect meets to join endlessly together and form a flexible junction to secure the one mono-tubular stent to yet another mono-tubular stent.

2. The stent of claim 1, wherein the interconnects bifurcate into a first arm and a second arm with the first arm defining the first surface and with the second arm defining the second surface.

3. The stent of claim 2, wherein the pair of intraconnects are positioned on diametrically opposing sides of the proximal end of the stent.

4. The stent of claim 3, comprising at least one reinforcing connector secured to the proximal end of the stent.

5. The stent of claim 4, wherein the intraconnects comprise a terminal connector secured to a flexible connector with the flexible connector secured to the proximal end of the stent.

6. The stent of claim 5, wherein the flexible connector comprises an elongated curved member.

7. A bifurcated stent apparatus, comprising:
    a first mono-tubular stent including at least a pair of first intraconnects secured to a proximal end of the first mono-tubular stent, the pair of first interconnects defining at least a first surface and a second surface forming a flexible junction to secure the first mono-tubular stent to a second mono-tubular stent and a third mono-tubular stent;
    the second mono-tubular stent including at least a pair of second intraconnects secured to a proximal end of the second mono-tubular stent, the pair of second interconnects defining at least a first surface and a second surface forming a flexible junction to secure the second mono-tubular stent to the first mono-tubular stent and the third mono-tubular stent, the second surface of each of the second pair of intraconnects secured to the first surface of one of the first pair of intraconnects of the first mono-tubular stent to secure the first mono-tubular stent to the second mono-tubular stent; and
    the third mono-tubular stent including at least a pair of third intraconnects secured to a proximal end of the third mono-tubular stent, the pair of third interconnects defining at least a first surface and a second surface forming a flexible junction to secure the third mono-tubular stent to the first mono-tubular stent and the second mono-tubular stent, the second surface of each of the third pair of intraconnects secured to the first surface of one of the second pair of intraconnects of the second mono-tubular stent to secure the second mono-tubular stent to the third mono-tubular stent to form a bifurcated stent apparatus.

8. A bifurcated stent apparatus, as in claim 7, further comprising a first flexible intraconnect having a first terminal connector secured to a first flexible connector with the first flexible connector secured to the proximal end of the first mono-tubular stent, a second flexible intraconnect having a second terminal connector secured to a second flexible connector with the second flexible connector secured to the proximal end of the second mono-tubular stent, and a third flexible intraconnect having a third terminal connector secured to the third flexible connector with the third flexible connector secured to the proximal end of the third mono-tubular stent.

9. A bifurcated stent apparatus, as in claim 8, wherein at least one of the first terminal connector, the second terminal connector and the third terminal connector further comprises a first surface and a second surface to secure to an adjacent terminal connector.

10. A bifurcated stent apparatus, as in claim 8 or 9, wherein the at least one of the first terminal connector, the second terminal connector and the third terminal connector further comprises the terminal connector bifurcating into a first arm and a second arm with the first arm defining a first surface and with the second arm defining a second surface with each of the first surface and the second surface configured to be secured to an adjacent terminal connector.

11. A stent apparatus, comprising:
a stent; and
a pair of intraconnects secured to a proximal end of the stent with the pair of intraconnects extending from the proximal end of the stent in an orientation substantially parallel to a longitudinal axis of the stent, the intraconnects defining a first surface and a second surface the first surface configured to secure the stent to a second stent and the second surface configured to secure the stent to a third stent.

12. A bifurcated stent comprising a first, a second and a third mono-tubular stents, each mono-tubular stent having a surface area and a pair of intraconnects positioned on a proximal end of each mono-tubular stent, the pairs of interconnects meeting to provide a flexible junction of the three mono-tubular stents in an arrangement relative to each other such that each member of each pair of intraconnects connects to a different mono-tubular stent.

13. The stent of claim 12, wherein each mono-tubular stent further comprises a pair of extended expandable members that increase the surface area of the bifurcated stent and improve strength and/or drug elution of the stent.

14. The stent of claim 13, wherein the extended expandable members extend from the proximal end of the stent to a point approaching an adjacent plane.

15. The stent of claim 12, wherein each of said pairs of intraconnects further comprise terminal connectors with a reinforcement member secured to a surface of each terminal connectors.

16. The stent of claim 12, further comprising a mono-tubular stent that may be directed outside a plane defined by the other two mono tubular stents.

17. The stent of claim 12, wherein the first intraconnect and the second and third intraconnects each have pairs of surfaces defining pointed proximal ends, the surface at the proximal end of the first intraconnect being configured to abut one proximal end surface of each of the second and third intraconnects, and the other proximal end surfaces of the second and third intraconnects being configured to abut and be the flexible junction of the three mono-tubular stents.

18. The stent of claim 17, wherein each intraconnect includes a flexible connector with terminal connectors, the flexible connectors are configured to be secured to the proximal end of a stent, each intraconnect is bifurcated at its proximal end to define arms defining at their ends spaced surfaces, and the surfaces of the intraconnects meet so that the bifurcated intraconnect ends form the flexible junction and are joined endlessly together.

19. The stent of claim 18, wherein the terminal connectors of the bifurcated ends of the intraconnects form the junction and are joined to define a triangular shape.

20. The stent of claim 18, wherein the terminal connectors of the bifurcated ends of the intraconnects form the junction and are joined to define a square shape.

21. The stent of claim 18, wherein the terminal connectors of the bifurcated ends of the intraconnects form the junction and are joined to define a looped shape.

22. The stent of claim 21, wherein the terminal connectors of the bifurcated ends of the intraconnects form the junction and are joined to define a circular shape.

23. The stent of claim 18, wherein distal regions of the intraconnects have flexibility imparted by a plurality of bends along their length.

24. The stent of claim 12, wherein each mono-tubular stent has the pair of intraconnects positioned on diametrically opposing sides thereof.

25. The stent of claim 24, wherein the mono-tubular stents are further connected by pairs of reinforcing connectors.

26. The stent of claim 12, wherein the intraconnects of the first, second and third mono-tubular stents are secured together in a generally radial arrangement to form a junction.

27. The stent of claim 12, wherein the mono-tubular stents are interconnected at welded meeting surfaces of the intraconnects.

28. The stent of claim 24, when in a collapsed state.

29. The stent of claim 24, when in an expanded state.

30. A method of making a bifurcated stent comprising a first, a second and a third mono-tubular stents, each mono-tubular stent having a surface area and a pair of intraconnects positioned on a proximal end of each mono-tubular stent, the pairs of interconnects meeting to provide a flexible junction of the three mono-tubular stents in an arrangement relative to each other such that each member of each pair of intraconnects connects to a different mono-tubular stent, which comprises:
independently fabricating the first, second and third mono-tubular stents;
positioning said mono-tubular stents so that said intraconnects meet for securing the mono-tubular stents together; and
welding the intraconnects together where they meet.

31. The method of claim 30, wherein the welding is a laser welding.

* * * * *